United States Patent [19]

Hussmann

[11] Patent Number: 4,754,074

[45] Date of Patent: Jun. 28, 1988

[54] PREPARATION OF DIALKYL KETONES FROM ALIPHATIC CARBOXYLIC ACIDS

[75] Inventor: Gregory P. Hussmann, Warrenville, Ill.

[73] Assignee: Amoco Corporation, Chicago, Ill.

[21] Appl. No.: 944,517

[22] Filed: Dec. 22, 1986

[51] Int. Cl.$^4$ ............................................. C07C 45/48
[52] U.S. Cl. ..................................... 568/319; 568/397
[58] Field of Search ..................... 568/319, 397, 398

[56] References Cited

U.S. PATENT DOCUMENTS

| | | | |
|---|---|---|---|
| 2,612,524 | 9/1952 | Zettlemoyer et al. | 568/319 |
| 2,697,729 | 12/1954 | Ohlson | 568/319 |
| 2,811,559 | 10/1957 | Chesrown et al. | 568/397 |
| 3,043,852 | 7/1962 | Mills | 568/354 |
| 3,075,016 | 1/1963 | Hammuberg et al. | 568/397 |
| 3,329,723 | 7/1967 | Muench et al. | 568/319 |
| 3,476,803 | 11/1969 | Pine | 568/379 |

OTHER PUBLICATIONS

Matsota et al, Chem. Abst.; vol. 74, #41830s (1971).
Schmeler et al, Chem. Abst., vol. 88, #6282g (1978).

*Primary Examiner*—James H. Reamer
*Attorney, Agent, or Firm*—Gunar J. Blumberg; William H. Magidson; Ralph C. Medhurst

[57] ABSTRACT

There is disclosed a method for the preparation of a dialkyl ketone from an aliphatic carboxylic acid in the presence of a catalyst comprising manganese dioxide on a support of catalytically active alumina. This method is a convenient way of making diethyl ketone from propionic acid.

16 Claims, No Drawings

PREPARATION OF DIALKYL KETONES FROM ALIPHATIC CARBOXYLIC ACIDS

CROSS-REFERENCE TO RELATED APPLICATION

This application is being filed concurrently in the U.S. Patent and Trademark Office with U.S. Ser. No. 944,516, which is directed to a method for preparing aromatic ketones, such as substituted benzophenones, by the ketonic decarboxylative coupling of substituted 3-cyclohexane carboxylic acids and subsequent dehydrogenation.

In addition, this application is being filed concurrently in the U.S. Patent and Trademark Office with U.S. Ser. No. 944,514, which is directed to the preparation of a benzophenone by the ketonic decarboxylative coupling of an aromatic carboxylic acid in the presence of a catalyst which is capable of catalyzing the conversion of an aromatic carboxylic acid to a benzophenone to provide a yield of at least 10% benzophenone and which comprises at least one oxide that is an oxide of an element having an atomic number of at least 60. Suitable catalysts are neodymium trioxide and a mixture of thorium dioxide and magnesium oxide.

BACKGROUND OF THE INVENTION

1. Field of the Invention

The present invention relates to the preparation of dialkyl ketones by a ketonic decarboxylative coupling of aliphatic carboxylic acids. More particularly, the present invention relates to the preparation of diethyl ketone by a ketonic decarboxylative coupling of propionic acid.

2. Description of the Prior Art

It has been shown that ketones can be formed via ketonic decarboxylation of carboxylic acids. For example, in an article in ZH. OBSHCH, KHIM., 30, 9, 2789 (1960), Rubinshtein et al, discussed the use of $ThO_2$, $CeO_2$, $CaCO_3$, $BaCO_3$, $ZnO_2$, and CdO as active catalysts for ketonization and the vapor-phase catalytic ketonization of acetic acid over carbonates of alkaline earth metals (Ca, Ba, Sr, and Mg). In KINET. KATAL., 2, 2, 172 (1961), Yakerson et al. investigated the kinetics of the thermal decomposition of lithium, sodium, and barium acetate to ketone and used the data to specify the mechanism of the vapor-phase ketonization of acetic acid and its decomposition to methane. In KINET. KATAL., 2, 6, 907 (1961), Yakerson et al. discussed the kinetics of vapor-phase catalytic ketonization of acetic acid over $TiO_2$, $ZrO_2$, $SnO_2$, $CeO_2$, and BeO. In IZV. AKAD. NAUK SSSR, No. 1, 83 (1966), Yakerson et al. discussed the catalytic ketonization of acetic acid over a mixed binary catalyst system of $ZrO_2$—$Al_2O_3$. In ZH, PRIKL. KHIM., 50, 2126 (1977), Shmelev et al. reported that diethyl ketone could be prepared by the ketonization of propionic acid in the presence of a catalyst of manganese dioxide supported on silica gel. In Japanese Publication Kokai Patent Application No. Sho 57(1982)–197237, Matsuoka discussed the preparation of a molecule of ketone from two molecules of a carboxylic acid over such catalysts as barium oxide, calcium oxide, lithium oxide, alumina, chromium oxide, manganese oxide, thorium oxide, gallium oxide, indium oxide, and oxides of various rare earth elements, which catalysts provide low conversions and selectivities, and disclosed the preparation of dialkyl ketones from carboxylic acids by means of a gas-phase contact reaction with a catalyst comprising zirconium oxide. Such catalyst can be supported on a carrier, such as alumina and silica gel. In West German Pat. No. 809,076, Godet disclosed the conversion of acetic acid to acetone in the presence of a catalyst of manganese oxide or an inorganic salt of manganese which is capable of forming an oxide by thermal decomposition, which catalyst may be deposited in fine distribution on a porous support, e.g., diatomaceous earth, glass wool, mineral wool, pumice, silica gel or activated carbon.

It has now been found that dialkyl ketones can be prepared from aliphatic carboxylic acids in the presence of a catalyst comprising manganese dioxide on alumina.

SUMMARY OF THE INVENTION

There is disclosed a process for the preparation of a dialkyl ketone from an aliphatic carboxylic acid in the presence of a catalyst comprising manganese dioxide on alumina. Typically, propionic acid can be treated at suitable temperatures in the vapor phase in the presence of a catalyst comprising manganese dioxide on alumina to form diethyl ketone.

DETAILED DESCRIPTION OF THE INVENTION

According to the present invention, there is provided a method for preparing a dialkyl ketone from an aliphatic carboxylic acid, which method comprises contacting a feed comprising said carboxylic acid in the vapor phase and under suitable conditions with a catalyst comprising manganese dioxide on a support of alumina. This method will provide the dialkyl ketone in conversions and selectivities that are sufficiently high for commercialization. Dialkyl ketones, such as diethyl ketones, can be used as solvents or as organic intermediates.

It has been found that a catalyst comprising manganese dioxide on a support of alumina can be used to catalyze the ketonic decarboxylative coupling of carboxylic acids to aliphatic ketones, specifically dialkyl ketones. The method proposed is suitable for the conversion of such aliphatic carboxylic acids as propionic acid and isobutyric acid to diethyl ketone and diisopropyl ketone, respectively. Therefore, the process of the present invention can be used to convert such aliphatic carboxylic acids as these to selected dialkyl ketones. Feeds containing one or more straight-chain or branched aliphatic carboxylic acids are suitable feedstocks for the process of the present invention. In addition, a feed comprising phenyl acetic acid is a suitable feed when producing 1,3-diphenyl-2-propanone.

The method of the present invention is conveniently conducted with a catalyst comprising manganese dioxide on a support of alumina. Such catalyst can be prepared conveniently by impregnating an alumina support with an aqueous solution of a water-soluble manganese compound. The impregnated material is then dried at a temperature within the range of about 100° C. to about 250° C. for a period of time within the range of about 5 hr to about 16 hr, preferably, at a temperature within the range of about 100° C. to about 150° C. for a period of about 5 hr to about 12 hr. The dried material is calcined in air at a temperature within the range of about 400° C. to about 600° C. for a period of time within the range of about 2 hr to about 20 hr, preferably, at a temperature within the range of about 475° C. to about 525° C. for a period of time within the range of about 10 hr to about 16 hr.

The alumina that is used in the preparation of the catalyst of the present invention is an alumina that is catalytically active and has a surface area within the range of about 5 m²/gm to about 400 m²/gm, preferably, within the range of about 50 m²/gm to about 250 m²/gm. Such aluminas can be purchased conveniently from various catalyst manufacturers.

The catalyst that is employed in the method of the present invention contains manganese dioxide in an amount within the range of about 5 wt% to about 30 wt%, based upon the total weight of catalyst. Preferably, the manganese dioxide is present within the range of about 10 wt% to about 25 wt%, based upon the total weight of the catalyst. More preferably, the catalyst contains manganese dioxide in an amount of about 19 wt% $MnO_2$.

The method or process of the present invention is conducted at suitable conditions, which include subatmospheric pressure and superatmospheric pressure, a temperature of up to about 500° C., or higher, and a contact time of as much as 10 sec. In the case of converting propionic acid to diethyl ketone, the pressure is maintained within the range of about 5 psi to about 200 psi, the temperature is maintained within the range of about 250° C. to about 500° C., and the contact time is held within the range of about 1 sec to about 10 sec. Preferably, the pressure is maintained within the range of about 5 psi to about 35 psi, the temperature is held within the range of about 325° C. to about 400° C., and the contact time is maintained within the range of about 3 sec to about 5 sec. Under such conditions, the reaction is carried out in the gas or vapor phase.

The catalyst of the method of the present invention does not lose its catalytic activity rapidly. In the event deactivation does occur, the catalyst can be regenerated conveniently by means of heating it in air or an oxygen-containing gas at a temperature and a time that are sufficient for coke removal, i.e., burning off the coke.

The main nonvolatile products of the process of the present invention are water and the dialkyl ketone(s), which can be separated mechanically to provide the dialkyl ketone(s) in a purity of greater than 90%. Solvent-grade pure dialkyl ketone can be prepared by means of simple distillation. In the case of the preparation of diethyl ketone, the simplicity of the entire process, the availability of the propionic acid, the reaction conditions, the catalysts, and the product recovery provide a convenient and efficient way to produce diethyl ketone.

The following examples are presented to facilitate the understanding of the present invention. These examples are presented for the purpose of illustration only and are not intended to limit the scope of the present invention.

EXAMPLES 1-10

A gas-phase minireactor was employed to test the ability of ten separate catalytic materials to convert propionic acid into diethyl ketone. Each of these tests, as well as those discussed hereinafter in Examples 11 through 20, was performed in the gas phase using a simple tube furnace reactor. Typically, 5 ml of the catalyst, in the form of 14/42-mesh material, were charged into a quartz reactor. The reactor was then placed in a single-zone, 12-inch Lindburg furnace controlled by a Eurotherm 919 system. Reactants were added at a rate of 0.09 ml/min or 0.10 ml/min by means of a Harvard Apparatus syringe drive. In Examples 1 through 17, the reactant feed rate was 0.09 ml/min, while in Examples 18 through 20, the reactant feed rate was 0.10 ml/min. A 10 ml/min flow of nitrogen was constantly swept through the reactor and catalyst bed during the reaction. The effluent from the reactor was collected in an ice-cooled receiving flask and analyzed.

The various unsupported materials that were employed as catalysts in these 10 examples were prepared by calcination of a commercially available oxide or calcination of a decomposable salt, such as nitrate, an acetate, or an oxalate. Typically, calcination conditions comprised a temperature within the range of about 500° C. to about 600° C. for a time of about 16 hrs.

Qualitative analysis of each reactor effluent was accomplished by gas chromatography or liquid chromatography. Reaction products were identified by gas chromatography-mass spectroscopy or by comparison of retention time with that of an authentic sample. Quantitative analysis was performed by gas chromatography using internal standards and predetermined response factors. Conversions and yields were determined directly from gas chromatographic area percents.

The reults of the tests performed in these examples are presented hereinafter in Table I. In Example 2, the alumina catayst was prepared from Degussa Aluminum Oxide C; in Example 3, the silica catalyst was prepared from Nalco 2327 silica; and in Example 7, the zirconia catalyst contained 2% alumina. The manganese dioxide catalyst in Example 8 was used as 5 ml of powder.

TABLE I

Ditheyl Ketone (DEK) from Propionic Acid (PA)

| Example | Catalyst | Temperature (°C.) | % PA Conversion | % DEK Yield | % DEK Selectivity |
|---|---|---|---|---|---|
| 1 | CaO | 365 | 36 | 12 | 33 |
| 2 | $Al_2O_3$ | 350 | 5 | 4 | 80 |
| 3 | $SiO_2$ | 350 | 0 | 0 | 0 |
| 4 | $Pb_2O_3$ | 365 | 79 | 52 | 66 |
| 5 | $Fe_2O_3$ | 350 | 20 | 19 | 95 |
| 6 | $ZrO_2$ | 365 | 99 | 92 | 93 |
| 7 | $ZrO_2$ | 350 | 99+ | 98 | 99 |
| 8 | $MnO_2$ | 365 | 91 | 80 | 88 |
| 9 | $ThO_2$ | 350 | 99+ | 98 | 99 |
| 10 | $Nd_2O_3$ | 350 | 64 | 63 | 98 |

The coupling of propionic acid to form diethyl ketone can be performed in the gas phase with many types of metal oxide catalysts. For example, alkaline earth metal oxides (CaO), transition metal oxides ($Fe_2O_3$), main group metal oxides ($Pb_2O_3$ and $Al_2O_3$), and rare earth metal oxides ($Nd_2O_3$) all convert propionic acid to diethyl ketone in low to moderate yields. However, as shown hereinabove, 90+% conversions and 88+% selectivities can be obtained with the +4 dioxides of zirconium, manganese, and thorium.

EXAMPLES 11-14

In these four examples, a supported catalyst of manganese dioxide was employed. In Examples 11 and 12, each of the catalysts contained in 19 wt% $MnO_2$ on a support of silica. In Example 8, the catalyst charge was made up of 5 ml of powder. In Example 11, the silica was a Nalco 2327 colloidal silica obtained from Nalco Chemical Company, and in Example 12, the silica was a Cabosil M-5 fumed silica obtained from Cabot Corporation. In Examples 13 and 14, each of the catalysts contained 19 wt% $MnO_2$ on a support of catalytically active alumina. In Example 13, the catalyst was obtained from Aldrich Chemical Company and possessed a surface area of 60 m²/gm. In Example 14, the alumina was an Aerogel 1000 alumina which had a surface area of 213 m²/gm and was obtained from the American Cyanamid Company.

Each of the supported catalysts was prepared by the incipient wetness technique. All supports were crushed and sieved to 14/42-mesh granules prior to impregnation. Impregnation of each of these supports was accomplished by dissolving a soluble metal salt in a volume of water equivalent to the pore volume of the support. This solution was then mixed with the support. The impregnated material was then dried overnight at a temperature of about 110° C. and subsequently calcined at a temperature within the range of about 500° C. to about 600° C. for a period of time of approximately 16 hr.

The tests and analyses conducted in these examples were carried out as described hereinabove for Examples 1 through 10.

The results obtained in Examples 11 through 14, as well as Example 8, are presented hereinbelow in Table II.

TABLE II
Diethyl Ketone from Propionic Acid
Effect of Catalyst Support

| Example | Catalyst | Surface Area (m²/g) | Temperature (°C.) | % Conversion (PA) | DEK % Yield | DEK % Selectivity |
|---|---|---|---|---|---|---|
| 8 | $MnO_2$ | — | 365 | 91 | 80 | 88 |
| 11 | 19% $MnO_2/SiO_2$ | 150 | 370 | 75 | 72 | 96 |
| 12 | 19% $MnO_2/SiO_2$ | 200 | 370 | 62 | 60 | 96 |
| 13 | 19% $MnO_2/Al_2O_3$ | 60 | 370 | 99+ | 96 | 96 |
| 14 | 19% $MnO_2/Al_2O_3$ | 213 | 370 | 99+ | 98 | 99 |

As demonstrated by the data in Table II, the catalyst comprising manganese dioxide on an alumina support provided significantly higher yields of diethyl ketone than either the catalyst of unsupported manganese dioxide or the catalysts comprising manganese dioxide on a support of silica. Furthermore, the yields of diethyl ketone that were obtained with the catalysts comprising manganese dioxide on an alumina support compared favorably with the best case of the catalysts comprising the unsupported +4 dioxides of thorium and zirconium. The data show also that the catalyst comprising manganese dioxide on alumina can have a wide range of surface areas and yet provide excellent yields of diethyl ketone. As evidenced hereinabove, a catalyst comprising manganese dioxide on a support of catalytically active alumina provides suitable and efficient conversion and selectivity of propionic acid to diethyl ketone.

EXAMPLES 15–17

Three tests were conducted with a catalyst comprising 19 wt% manganese dioxide on a support of Aerogel 1000 alumina. In each case, the catalyst was tested for its ability to convert propionic acid to diethyl ketone. The catalyst was prepared as described hereinabove. These three tests, namely, those in Examples 14, 15, and 16, were carried out at different reaction temperatures to aid in defining the effect of temperature on the conversion of propionic acid to diethyl ketone and were conducted as described hereinabove in Examples 1 through 10. In addition, a catalyst comprising 9 wt% manganese dioxide on an alumina support was tested in Example 17 to demonstrate its performance when converting propionic to diethyl ketone. The results obtained in Examples 14 through 17 are presented hereinbelow in Table III.

TABLE III
Diethyl Ketone from Propionic Acid
Effect of Temperature

| Example | Catalyst | Temperature (°C.) | % Conversion (PA) | DEK % Yield | DEK % Selectivity |
|---|---|---|---|---|---|
| 14 | 19% $MnO_2/Al_2O_3$ | 370 | 99+ | 98 | 99 |
| 15 | 19% $MnO_2/Al_2O_3$ | 330 | 53 | 52 | 99 |
| 16 | 19% $MnO_2/Al_2O_3$ | 350 | 97 | 96 | 99 |
| 17 | 9% $MnO_2/Al_2O_3$ | 370 | 52 | 51 | 99 |

It appears desirable to utilize temperatures within the range of about 350° C. to about 370° C. Preferably, the catalyst should contain about 19 wt% manganese dioxide, based upon the total weight of the catalyst. If the temperature is lower than the above-suggested range or if the catalyst contains a smaller amount of manganese dioxide, the conversion of the propionic acid to diethyl ketone will be sharply reduced.

EXAMPLES 18–20

In each of these examples, aliphatic acids other than propionic acid were reacted in the presence of a catalyst comprising 19 wt% manganese dioxide on a support of catalytically active alumina. The other reactants that were tested were phenyl acetic acid, isobutyric acid, and trimethyl acetic acid. Each of these tests was conducted as described hereinabove for Examples 1 through 10. The test results obtained from these examples, along with those from Example 14, are presented hereinafter in Table IV.

TABLE IV
Coupling of Aliphatic Acids with 19% $MnO_2/Al_2O_3$

| Example | Acid | Temperature (°C.) | Product | % Conversion | % Yield | % Selectivity |
|---|---|---|---|---|---|---|
| 14 | Propionic | 370 | Diethyl ketone | 99 | 98 | 99 |
| 18 | Phenyl Acetic | 370 | 1,3-diphenyl-2-propanone | 99 | 80 | 81 |
| 19 | Isobutyric | 370 | Diisopropyl ketone | 85 | 69 | 81 |
| 20 | Trimethyl Acetic | 370 | Diisobutyl ketone | — | 0 | 0 |

The results of these tests demonstrate that for a volatile acid which contains at least one alpha-hydrogen, a high yield of the ketone coupling product can be obtained. Both propionic acid and phenyl acetic acid contain two alpha-hydrogens. The propionic acid provided a 98% yield of diethyl ketone, while the phenyl acetic acid provided an 80% yield of 1,3-diphenyl-2-propanone. Furthermore, isobutyric acid, which contains one alpha-hydrogen, coupled to form diisopropyl ketone in a yield of 69% under similar reaction conditions. On the other hand, trimethyl acetic acid, which contains no alpha-hydrogens, did not couple to form the expected ketone in detectable yield. It appears that there is a correlation between the number of alpha-hydrogens in the carboxylic acid reactant and the ability of that reactant to undergo ketonic decarboxylation. In view of this, the method of the present invention is a method for converting into a dialkyl ketone a carboxylic acid that is a volatile acid and that contains at least one alpha-hydrogen.

What is claimed is:

1. A method for preparing an aliphatic dialkyl ketone from a carboxylic acid selected from the group consisting of straight chain aliphatic carboxylic acids, branched chain aliphatic carboxylic acids and phenyl acetic acid, which method comprises contacting a feed comprising said carboxylic acid with a manganese dioxide on alumina catalyst in the vapor phase at a temperature within the range of about 250° C. to about 500° C., a pressure within the range of about 5 psi to about 200 psi, and a contact time within the range of about 1 sec to about 10 sec. wherein the manganese dioxide on alumina catalyst is prepared by the incipient wetness technique.

2. The method of claim 1, wherein said carboxylic acid contains at least 1 alpha-hydrogen and is a volatile acid.

3. The method of claim 1, wherein said catalyst contains manganese dioxide in an amount within the range of about 5 wt% to about 30 wt%, based upon the total weight of the catalyst, on a support of catalytically active alumina having a surface area within the range of about 5 m$^2$/gm to about 400 m$^2$/gm.

4. The method of claim 2, wherein said carboxylic acid contains 2 alpha-hydrogens.

5. The method of claim 2, wherein said carboxylic acid is selected from the group consisting of isobutyric acid, propionic acid, and phenyl acetic acid.

6. The method of claim 4, wherein said carboxylic acid is selected from the group consisting of propionic acid and phenyl acetic acid.

7. The method of claim 5, wherein said catalyst contains manganese dioxide in an amount within the range of about 5 wt% to about 30 wt%, based upon the total weight of the catalyst, on a support of catalytically active alumina having a surface area within the range of about 5 m$^2$/gm to about 400 m$^2$/gm.

8. The method of claim 6, wherein said catalyst contains manganese dioxide in an amount within the range of about 5 wt% to about 30 wt%, based upon the toal weight of the catalyst, on a support of catalytically active alumina having a surface area within the range of about 5 m$^2$/gm to about 400 m$^2$/gm.

9. The method of claim 5 wherein said catalyst contains manganese dioxide in an amount within the range of about 5 wt% to about 30 wt%, based upon the total weight of the catalyst, on a support of catalytically active alumina having a surface area within the range of about 5 m$^2$/gm to about 400 m$^2$/gm.

10. The method of claim 6 wherein said catalyst contains manganese dioxide in an amount within the range of about 5 wt% to about 30 wt%, based upon the total weight of the catalyst, on a support of catalytically active alumina having a surface area within the range of about 5 m$^2$/gm to about 400 m$^2$/gm.

11. The method of claim 9, wherein said temperature is within the range of about 325° C. to about 400° C., pressure is within the range of about 5 psi to about 35 psi, and contact time is within the range of about 3 sec to about 5 sec.

12. The method of claim 10, wherein said temperature is within the range of about 325° C. to about 400° C., pressure is within the range of about 5 psi to about 35 psi, and contact time is within the range of about 3 sec to about 5 sec.

13. The method of claim 11, wherein said catalyst contains manganese dioxide in an amount within the range of about 10 wt% to about 25 wt%, based upon the total weight of the catalyst, on a support of catalytically active alumina having a surface area within the range of about 50 m$^2$/gm to about 250 m$^2$/gm.

14. The method of claim 12, wherein said catalyst contains manganese dioxide in an amount within the range of about 10 wt% to about 25 wt%, based upon the total weight of the catalyst, on a support of catalytically active alumina having a surface area within the range of about 50 m$^2$/gm to about 250 m$^2$/gm.

15. The method of claim 14, wherein said carboxylic acid is propionic acid and is converted to diethyl ketone.

16. The method of claim 15, wherein said catalyst contains about 19 wt% MnO$_2$, based upon the total weight of said catalyst.

* * * * *